(12) United States Patent
Couturier et al.

(10) Patent No.: US 8,324,214 B2
(45) Date of Patent: Dec. 4, 2012

(54) 1,3-DIHYDRO-2H-PYRROLO[3,2-B]PYRIDIN-2-ONE DERIVATIVES, PREPARATION THEREOF AND THERAPEUTIC USES THEREOF

(75) Inventors: Cedric Couturier, Paris (FR); Loic Foulon, Paris (FR); Claudine Serradeil-Le Gal, Paris (FR); Gerard Valette, Paris (FR)

(73) Assignee: Sanofi, Paris (FR)

( * ) Notice: Subject to any disclaimer, the term of this patent is extended or adjusted under 35 U.S.C. 154(b) by 236 days.

(21) Appl. No.: 12/905,287

(22) Filed: Oct. 15, 2010

(65) Prior Publication Data

US 2011/0071160 A1 Mar. 24, 2011

Related U.S. Application Data

(63) Continuation of application No. PCT/FR2009/000456, filed on Apr. 17, 2009.

(30) Foreign Application Priority Data

Apr. 21, 2008 (FR) ........................ 08 02195

(51) Int. Cl.
- A61K 31/496 (2006.01)
- A61K 31/437 (2006.01)
- C07D 471/04 (2006.01)
- A61P 15/06 (2006.01)
- A61P 15/00 (2006.01)
- A61P 15/08 (2006.01)
- A61P 13/06 (2006.01)
- A61P 9/12 (2006.01)
- A61P 25/00 (2006.01)
- A61P 3/10 (2006.01)

(52) U.S. Cl. .............. 514/253.04; 514/300; 546/113; 544/362

(58) Field of Classification Search .............. 546/113; 544/362; 514/253.04, 300
See application file for complete search history.

(56) References Cited

U.S. PATENT DOCUMENTS 5,618,833 A 4/1997 Foulon et al.

FOREIGN PATENT DOCUMENTS

| AU | 684791 | 1/1998 |
|---|---|---|
| EP | 0636608 A1 | 2/1995 |
| EP | 0469984 B1 | 10/1995 |
| WO | WO 93/15051 | 8/1993 |
| WO | WO 95/18105 | 7/1995 |
| WO | WO 97/15556 | 5/1997 |
| WO | WO 98/25901 | 6/1998 |
| WO | WO 01/55130 | 8/2001 |
| WO | WO 01/55134 | 8/2001 |
| WO | WO 01/64668 | 9/2001 |
| WO | WO 01/98295 | 12/2001 |
| WO | WO 03/006407 | 1/2003 |
| WO | WO 2006/080574 | 8/2006 |
| WO | WO 2008/025735 | 3/2008 |
| WO | WO 2009/133314 A1 | 11/2009 |

OTHER PUBLICATIONS

Hulme et al., Bioorganic & Medicinal Chemistry Letters (1998), 8(2), 175-178.*
Woll, P. J., et. al., Multiple Neuropeptities Mobilise Calcium in Small Cell Lung Cancer: Effects of Vasopressin Bradykinin, Choleoystokinin, Galanin and Neurotensin, Biochemical and Biophysical Research Communications, pp. 66-73, vol. 164, No. 1, (1989).
Aresenijevic, Y., et. al., Vasopressin-Binding Sites in the Pig Putuitary Gland: Competition by Novel Vasopressin Antagonists Suggest the Existence of an Unusual Receptor Subtype in the Anterior Lobe, J. Endocrinology, vol. 141, pp. 383-391, (1994).
Bernardini, et. al., In Vivo and in Vitro Effects of Arginine-Vasopressin Receptor Antagonists on the Hypothalamic Pituitary-Adrenal Axis in the Rat, Neuroendocrinology, vol. 60. pp. 503-508, (1994).
Berthereat, J., et. al., Ectopic Expression of the Pituitary V3 Vasopressin Receptor Reveals New Aspects of the Ectopic ACTH Syndrome, Eur. J. Endocrino., (1996), vol. 135, pp. 173-174.

(Continued)

*Primary Examiner* — Niloofar Rahmani
(74) *Attorney, Agent, or Firm* — Ronald G. Ort

(57) ABSTRACT

The subject matter of the present invention are compounds corresponding to formula (I):

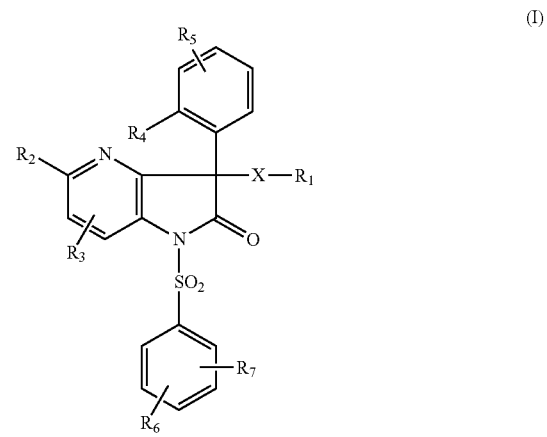

in which: X is an unsubstituted or substituted divalent ($C_1$-$C_5$)alkylene radical; $R_1$ is an —$NR_8R_9$ group; or an unsubstituted or substituted piperidin-3-yl or piperidin-4-yl radical; $R_2$ is a hydrogen atom, a halogen atom, an Alk group or an OAlk group; $R_3$ is a hydrogen atom, a halogen atom, an Alk group or an OAlk group; $R_4$ is a hydrogen atom, a halogen atom, an Alk group, a hydroxyl or an OAlk group; and $R_5$ is a hydrogen atom, a halogen atom, an Alk group, a hydroxyl or an OAlk group.

6 Claims, No Drawings

OTHER PUBLICATIONS

Birnbaumer, M., et. al., Molecular Cloning of the Receptor for Human Antidiuretic Hormone, Nature, vol. 357 (1992), pp. 333-335.

Dickstein, G., et, al., Plasma Corticotropin and Cortisol Responses to Ovine Corticotropin-Releasing Hormone (CRH), Arginine Vasopressin (AVP), CRH plus AVP, and CRH plus Metyrapone in Patients with Cushing's Disease, Journal of Clinical Endocrinology and Metabolism. vol. 81, No. 8, pp. 2934-2941, (1996).

Elands, et. al., 125I-Labelled D(CH2)5[Tyr(Me)2,Thr4,Tyr-NH29]OVT: A Selective Oxytocin Receptor Ligand, European Journal of Pharmacology, vol. 147, pp. 197-207, (1987).

Gillies, G. E., et. al., Corticotropin Releasing Activity of the New CRF is Potentiated Several Times by Vasopressin, Nature, vol. 299, pp. 355-357, (1982).

Grazzini, E., et. al., Molecular and Functional Characterization of V1b Vasopressin Receptor in Rat Adrsnal Medulla, Endocrinology, vol. 137, No. 9, pp. 3906-3914, (1996).

Grazzini, E., et al., Vasopressin Receptors in Human Adrenal Medulla and Pheochromocytoma, The Journal of Clinical Endocrinology & Metabolism, (1999), vol. 84, pp. 2195-2203.

Guillon, G., et. al, Vasopressin Stimulates Steroid Secretion in Human Adrenal Glands; Comparison with Angiotensin-II Effect, Endocrinology, vol. 136, No. 3, pp. 1265-1295, (1995).

Jard, S., et al., Vasopressin Antagonist Allow Demonstration of a Novel Type of Vasopressin Receptor in the Rat Adenohypophysis, Molecular Pharmacology, vol. 30, pp. 171-177, (1986).

Jard, S., et. al., Vasopressin and Oxytocin Receptors: An Overview, Progress in Endocrinology, (1968), pp. 183-1188.

Keyzer, Y. D., et. al., Cloning and Characterization of the Human V3 Pituitary Vasopressin Receptor, FEBS Letters, vol. 356, (1994), pp. 215-220.

Laszlo, F.A., et. al., Pharmacology and Clinical Perspectives of Vasopressin Antagonists, Pharmacology Rev., (1991), vol. 43, No. 1, pp. 73-108.

Lee, B., et al., Effect of AVP and Oxytocin on Insulin Release: Involvement of V1b Receptors. Am. J. Physiol., vol. 269, (Endocrinol. Metab. 32), pp. E1095-E1100, (1995).

Lolait, S. J., et. al., Extrapituitary Expression of the Rat V1b Vasopressin Receptor Gene, Proc. Natl. Aca. Sci USA, Neurobiology, vol. 92, pp. 6783-6787, (1995).

Manning, M., et al., Discovery, Development, and Some Uses of Vasopressin and Oxytocin Antagonists, J. Lab. Clin. Med., (1989), vol. 114, No. 6, pp. 617-632.

Mazzocchi, G., et. al., Arginine-Vasopressin Stimulates CRH and ACTH Release by Rat Adrenal Medulla, Acting Via the V1 Receptor Subtype and a Protein Kinase C-Dependent Pathway, Peptides, vol. 18, No, 2, pp. 191-195, (1997).

Saito, M., et. al., Molecular Cloning and Characterization of Rat V1B Vasopressin Receptor: Evidence for its Expression in Extra-Pituitary Tissues, Biochemical and Biophysical Research Communications, vol. 212, No. 3, (1995), pp. 751-757.

Schwartz, J, et. al., A Potent New Synthetic Analog of Vasopressin With Relative Agonist Specificity for The Pituitary, Endocrinology, vol. 129, No. 2, pp. 1107-1109, (1991).

Serradeil-Le Gal, C., et. al., Biochemical and Pharmacological Properties of SR 49059, A New Potent: Nonpeptide Antagonist of Rat and Human Vasopressin V1a Receptors, J. Clin, Invest., vol. 92, pp. 224-231, (1993).

Sugimoto, T., et. al., Molecular Cloning and Functional Expression of a CDNA Encoding the Human V1b Vasopressin Receptor, The Journal of Biological Chemistry, vol. 269, No. 43, (1994), pp. 27088-27092.

Suluvan, E., et. al., Measurement of [Ca2+] Using the Fluorometric Imaging Plate Reader (FLIPR), Methods in Molecular Biology, vol. 114, pp. 125-133, (1999).

Thibonnier, M., et. al., Molecular Cloning, Sequencing, and Functional Expression of a CDNA Encoding the Human V1a Vasopressin Receptor, The Journal of Biological Chemistry, vol. 269, No. 5, pp. 3304-3310, (1994).

Ventura, M. A., et. al., Gene and cDNA Cloning and Characterization of the Mouse V3/V1b Pituitary Vasopressin Receptor, Journal of Molecular Endocrinology, (1999), vol. 22, pp. 251-260.

Wittert, G. A., et. al., Arginine Vasopressin in Cushing's Disease, The Lancet (1990), vol. 335, pp. 991-994.

\* cited by examiner

1,3-DIHYDRO-2H-PYRROLO[3,2-B]PYRIDIN-2-ONE DERIVATIVES, PREPARATION THEREOF AND THERAPEUTIC USES THEREOF

FIELD OF THE INVENTION

The present invention relates to novel 1,3-dihydro-2H-pyrrolo[3,2-b]pyridin-2-one derivatives, to their preparation and to their therapeutic application.

The compounds according to the present invention exhibit a high affinity and a high selectivity for the human $V_{1a}$ receptors or, for some compounds, for both the human $V_{1a}$ and $V_{1b}$ receptors for arginine-vasopressin (AVP).

BACKGROUND OF THE INVENTION

AVP is a hormone known for its antidiuretic effect and its effect in regulating arterial pressure. It stimulates several types of receptor: $V_1$ ($V_{1a}$, $V_{1b}$), $V_2$. These receptors are located in particular in the liver, vessels (coronary, renal, cerebral), platelets, kidney, uterus, adrenal glands, pancreas, central nervous system and pituitary gland. AVP thus exerts cardiovascular, hepatic, pancreatic, antidiuretic and platelet-aggregating effects and effects on the central and peripheral nervous system, and on the uterine sphere.

The location of various receptors is described in: S. JARD et al., Vasopressin and oxytocin receptors: an overview, in Progress in Endocrinology. H. IMURA and K. SHIZURNE ed., Experta Medica, Amsterdam, 1988, 1183-1188, and in the following articles: J. Lab. Clin. Med., 1989, 114 (6), 617-632 and Pharmacol. Rev., 1991, 43 (1), 73-108.

More particularly, the AVP $V_{1a}$ receptors are located in numerous peripheral organs and in the brain. They have been cloned in rats and humans and they regulate the majority of the known effects of the AVP: platelet aggregation; uterine contractions; contraction of the vessels; contraction of renal mesangial cells, the secretion of aldosterone, cortisol, CRF (corticotropin-releasing factor) and adrenocorticotrophic hormone (ACTH); hepatic glycogenolysis, cell proliferation and the main central effects of AVP (hypothermia, memory, anxiety, affiliation and the like).

The adrenocortex is also rich in $V_{1a}$ receptors involved in the production of gluco- and mineralocorticoids (aldosterone and cortisol). Via these receptors, AVP (circulating or synthesized locally) can induce a production of aldosterone with an efficiency comparable to that of angiotensin II (G. GUILLON et al., Endocrinology, 1995, 136 (3), 1285-1295). Cortisol is a potent regulator of the production of ACTH, the stress hormone.

Recent studies have shown that the adrenal glands were capable of directly releasing CRF and/or ACTH via the activation of the $V_{1a}$ and/or $V_{1b}$ receptors carried by the cells of the medulla (G. MAZZOCCHI et al., Peptides, 1997, 18 (2), 191-195; E. GRAZZINI et al., J. Clin. Endocrinol. Metab., 1999, 84 (6), 2195-2203).

The $V_{1a}$ receptors are also a more specific marker for small-cell lung cancers (SCLC) (P. J. WOLL et al., Biochem. Biophys. Res. Commun., 1989, 164 (1), 66-73). Thus, the compounds according to the present invention are obvious diagnostic tools and offer a novel therapeutic approach for controlling the proliferation of these tumours and their detection, even at an early stage (radiolabelling; SPECT, Single Photon Emission Computed Tomography; PET Scan, Positron Emission Tomography Scanner).

The $V_{1b}$ receptors were initially identified in the adenohypophysis of various animal species (rat, pig, cow, sheep and the like) including in humans (S. Jard et al., Mol. Pharmacol., 1986, 30, 171-177; Y. Arsenijevic et al., J. Endocrinol., 1994, 141, 383-391; J. Schwartz et al., Endocrinology, 1991, 129 (2), 1107-1109; Y. de Keyser et al., FEBS Letters, 1994, 356, 215-220) where they stimulate the release of adrenocorticotrophic hormone by AVP and potentiate the effects of CRF on the release of ACTH (G. E. Gdjjes et al., Nature, 1982, 299, 355). In the hypothalamus, the $V_{1b}$ receptors induce a direct release of CRF (Neuroendocrinology, 1994, 60, 503-508) and are, in these various respects, involved in stress situations.

These $V_{1b}$ receptors have been cloned into rats, human and mice (Y. de Keyser, FEBS Letters, 1994, 356, 215-220; T. Sugimoto et al., J. Biol. Chem., 1994, 269 (43), 27088-27092; M. Saito et al., Biochem. Biophys. Res. Commun., 1995, 212 (3), 751-757; S. J. Lolait et al., Neurobiology, 1996, 92, 6783-6787; M. A. Ventura et al., Journal of Molecular Endocrinology, 1999, 22, 251-260) and various studies (in situ hybridization, PCR, Polymerase Chain Reaction, and the like) reveal a ubiquitous location of these receptors in various central tissues (brain, hypothalamus and adenohypophysis, in particular) and peripheral tissues (kidney, pancreas, adrenal glands, heart, lungs, intestine, stomach, liver, mesentery, bladder, thymus, spleen, uterus, retina, thyroid, and the like) and in some tumours (hypophysial tumours, pulmonary tumours and the like), suggesting a broad biological and/or pathological role of these receptors and potential involvement in various diseases.

By way of examples, in rats, studies have shown that AVP, via the $V_{1b}$ receptors, regulates the endocrine pancreas, stimulating the secretion of insulin and glucagon (B. Lee et al., Am. J. Physiol. 269 (Endocrinol. Metab. 32): E1095-E1100, 1995) or the production of catecholamines in the medullo-adrenal which is the seat of local synthesis of AVP (E. Grazzini et al., Endocrinology, 1996, 137 (a), 3906-3914). Thus, in the latter tissue, AVP, via these receptors, is thought to have a crucial role in some types of adrenal pheochromocytomas which secrete AVP and thereby induce sustained production of catecholamines responsible for hypertension resistant to antagonists of the angiotensin II receptors and converting enzyme inhibitors.

The $V_{1b}$ receptors are also considered as a marker for ACTH-secreting tumours such as certain pituitary tumours, certain bronchial carcinomas (SCLC, Small Cell Lung Cancers), pancreatic carcinomas, adrenal carcinomas and thyroid carcinomas, resulting in Cushing's syndrome in some cases (J. Bertherat et al., Eur. J. Endocrinol., 1996, 135, 173; G. A. Wuinert et al., Lancet, 1990, 335, 991-994; G. Dickstein et al., J. Clin. Endocrinol. Metab., 1996, 81 (8), 2934-2941).

The abundant presence of the messenger for the $V_{1b}$ receptors at the stomach and intestinal level suggests an involvement of AVP via this receptor on the release of gastrointestinal hormones such as cholecystokinin, gastrin or secretin (T. Sugimoto et al., Molecular cloning and functional expression of $V_{1b}$ receptor gene, in Neurohypophysis: Recent Progress of Vasopressin and Oxytocin Research; T. Saito, K. Kurosawa and S. Yoshida, ed., Elsevier Science, 1995, 409413).

1,3-Dihydro-2H-indol-2-one derivatives have been described in some patent applications as ligands for the arginine-vasopressin and/or oxytocin receptors: there may be mentioned patent applications WO 93/15 051, EP 636 608, EP 636 609, WO 97/15 556, WO 98/25 901, WO 01/55 130, WO 01/55 134, WO 01/64 668, WO 01/98 295, WO 03/008 407, WO 06/080 574, WO 08/025,735.

International application WO 95/18 105 relates to compounds of formula:

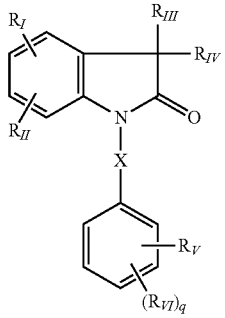

(A)

in which in particular:
X represents $SO_2$;
$R_I$, $R_{II}$, $R_{III}$, $R_{IV}$, $R_V$, $R_{VI}$ and q have different values.

The compounds of formula (A) have affinity for in general the vasopressin and/or oxytocin receptors. In addition, this application describes no example in which the 4-position of the indol-2-one ring is occupied by a nitrogen atom and $R_{IV}$ is still attached at the 3-position of the indol-2-one ring by a nitrogen atom.

In particular 3-[4-[[5,6-dichloro-3-(2-chlorophenyl)-2-oxo-3-[(2-piperidin-4-ylethyl)amino]-2,3-dihydro-1H-indol-1-yl]sulphonyl]phenyl]-1,1-diethylurea (compound α) is described in Example 220 and 3-[4-[[5-chloro-3-(2-chlorophenyl)-6-methyl-2-oxo-3-[(2-piperidin-4-ylethyl)amino]-2,3-dihydro-1H-indol-1-yl]sulphonyl]phenyl]-1-diethylurea (compound β) is described in Example 277 of WO 95/018 105.

Compound α exhibits good affinity for the human $V_{1a}$ receptors for AVP, but also for the human $V_2$ receptors for AVP and the oxytocin receptors; it is not therefore selective for the human $V_{1a}$ receptors for AVP and for the human $V_{1b}$ receptors for AVP.

Compound β exhibits good affinity for the human $V_{1a}$ receptors for AVP, but also for the human $V_2$ receptors for AVP; it is not therefore selective for the human $V_{1a}$ receptors for AVP and for the human $V_{1b}$ receptors for AVP.

DESCRIPTION OF THE INVENTION

Novel compounds have now been found which exhibit high affinity and high selectivity for the human $V_{1a}$ receptors for AVP and which are antagonists of the said receptors and some compounds further exhibit high affinity for the human $V_{1b}$ receptors for AVP.

The subject of the invention is compounds corresponding to formula (I)

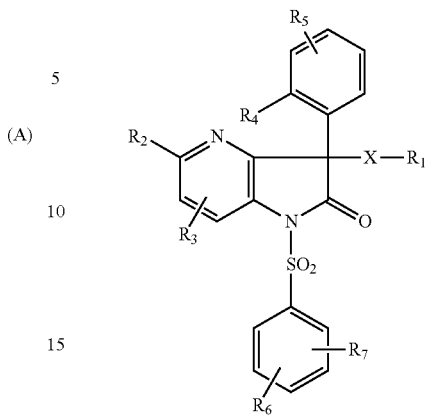

(I)

in which:
X represents a bivalent $(C_1-C_5)$alkylene radical that is unsubstituted or substituted once or several times on a carbon atom with a fluorine atom or with a $(C_1-C_3)$alkyl;
$R^1$ represents:
  a group $—NR_8R_9$;
  a piperidin-3-yl or piperidin-4-yl radical that is unsubstituted or substituted once or several times with a $(C_1-C_4)$alkyl, a $(C_3-C_5)$cycloalkyl, it being possible for the carbon atoms to also be substituted with one or more fluorine atoms;
$R_2$ represents a hydrogen atom, a halogen atom, an Alk group, an OAlk group;
$R_3$ represents a hydrogen atom, a halogen atom, an Alk group, an OAlk group;
$R_4$ represents a hydrogen atom, a halogen atom, an Alk group, a hydroxyl, an OAlk group;
$R_5$ represents a hydrogen atom, a halogen atom, an Alk group, a hydroxyl, an OAlk group;
$R_6$ represents a hydrogen atom, a halogen atom, an Alk group, a hydroxyl, an OAlk group;
$R_7$ represents a hydrogen atom, a halogen atom, an Alk group, a hydroxyl, an OAlk group;
$R_8$ and $R_9$ each independently represent a hydrogen atom or a $(C_1-C_4)$alkyl;
or alternatively $R_8$ and $R_9$, together with the nitrogen atom to which they are attached, constitute a heterocyclic radical chosen from: azetidin-1-yl, pyrrolidin-1-yl, piperidin-1-yl, morpholin-4-yl, thiomorpholin-4-yl, piperazin-1-yl or perhydroazepin-1-yl, the said heterocyclic radical being unsubstituted or substituted once or several times with an amino, a hydroxyl, a $(C_1-C_4)$alkyl, a $(C_3-C_5)$cycloalkyl, a $(C_1-C_4)$alkoxy, it being possible for the carbon atoms to also be substituted with one or more fluorine atoms;
Alk represents a $(C_1-C_4)$alkyl that is unsubstituted or substituted once or several times with a fluorine atom.

The compounds of formula (I) may contain one or more asymmetric carbon atoms. They may therefore exist in the form of enantiomers or diastereoisomers. These enantiomers, diastereoisomers and mixtures thereof, including the racemic mixtures, form part of the invention.

The compounds of formula (I) may exist in the form of bases or addition salts with acids. Such addition salts form part of the invention.

These salts are advantageously prepared with pharmaceutically acceptable acids, but the salts of other acids useful for the purification or isolation of the compounds of formula (I) also form part of the invention.

According to the present invention, the N-oxides of the compounds containing an amine or a nitrogen atom also form part of the invention.

The expression halogen atom is understood to mean a bromine, chlorine, fluorine or iodine atom.

The expression $(C_1-C_3)$alkyl or respectively $(C_1-C_4)$alkyl is understood to mean a linear or branched alkyl radical of one to three carbon atoms or respectively of one to four carbon atoms, such as the methyl, ethyl, propyl, isopropyl, butyl, isobutyl, sec-butyl or tert-butyl radical.

The expression $(C_1-C_5)$alkylene is understood to mean a bivalent radical of one to five carbon atoms such as the methylene, ethylene, trimethylene or tetramethylene radical, or the pentamethylene radical.

The expression $(C_3-C_5)$cycloalkyl is understood to mean a cyclopropyl, cyclobutyl or cyclopentyl radical.

The expression $(C_1-C_4)$alkoxy is understood to mean a linear or branched alkoxy radical of one to four carbon atoms such as the methoxy, ethoxy, propoxy, isopropoxy, butoxy, sec-butoxy or tert-butoxy radical.

According to the present invention, preference is given to the compounds of formula (I) in which:
  X represents a bivalent $(C_3-C_4)$ alkylene radical that is unsubstituted or substituted once or several times on a carbon atom with a fluorine atom or with a $(C_1-C_3)$ alkyl;
  $R_1$ represents:
    a group —$NR_8R_9$;
    a piperidin-4-yl radical;
  $R_2$ represents an Alk group, an OAlk group;
  $R_3$ represents a hydrogen atom;
  $R_4$ represents a halogen atom;
  $R_5$ represents a hydrogen atom;
  $R_6$ represents a halogen atom, an OAlk group;
  $R_7$ represents a hydrogen atom, an Alk group, an OAlk group;
  $R_8$ and $R_9$ together with the nitrogen atom to which they are attached constitute a heterocyclic radical chosen from: piperidin-1-yl, piperazin-1-yl, the said heterocyclic radical being unsubstituted or substituted once or twice with a fluorine atom, an amino, a hydroxyl, a methyl;
  Alk represents a $(C_1-C_4)$alkyl that is unsubstituted or substituted once or several times with a fluorine atom;
in the form of a base or an addition salt with an acid.

In particular, preference is given to the compounds of formula (I) in which:
  X represents a bivalent trimethylene or tetramethylene radical;
  $R_1$ represents:
    a piperidin-1-yl, a piperazin-1-yl, a 4-methylpiperazin-1-yl;
    a piperidin-4-yl;
  $R_2$ represents a methyl, a methoxy;
  $R_3$ represents a hydrogen atom;
  $R_4$ represents a fluorine atom;
  $R_5$ represents a hydrogen atom;
  $R_6$ represents a chlorine atom, a methoxy, an isopropoxy, a difluoromethoxy;
  $R_7$ represents a hydrogen atom, a methyl, a methoxy;
in the form of a base or an addition salt with an acid.

Among the compounds of formula (I) which are the subject of the invention, the following compounds may be mentioned in particular:

3-(2-fluorophenyl)-1-[(4-isopropoxyphenyl)sulphonyl]-5-methoxy-3-(3-piperazin-1-ylpropyl)-1,3-dihydro-2H-pyrrolo[3,2-b]pyridin-2-one;

3-(2-fluorophenyl)-1-[(4-isopropoxyphenyl)sulphonyl]-5-methoxy-3-(3-piperazin-1-ylpropyl)-1,3-dihydro-2H-pyrrolo[3,2-b]pyridin-2-one;

3-(2-fluorophenyl)-5-methoxy-1-[(3-methoxyphenyl)sulphonyl]-3-(3-piperazin-1-ylpropyl)-1,3-dihydro-2H-pyrrolo[3,2-b]pyridin-2-one;

1-[(3-chlorophenyl)sulphonyl]-3-(2-fluorophenyl)-5-methoxy-3-(3-piperazin-1-ylpropyl)-1,3-dihydro-2H-pyrrolo[3,2-b]pyridin-2-one;

3-(2-fluorophenyl)-1-[(4-isopropoxyphenyl)sulphonyl]-5-methoxy-3-(3-piperidin-1-ylpropyl)-1,3-dihydro-2H-pyrrolo[3,2-b]pyridin-2-one;

3-(2-fluorophenyl)-1-[(4-isopropoxyphenyl)sulphonyl]-5-methoxy-3-(3-piperidin-1-ylpropyl)-1,3-dihydro-2H-pyrrolo[3,2-b]pyridin-2-one;

3-(2-fluorophenyl)-5-methoxy-1-[(3-methoxyphenyl)sulphonyl]-3-(3-piperidin-1-ylpropyl)-1,3-dihydro-2H-pyrrolo[3,2-b]pyridin-2-one, isomer;

1-{[4-(difluoromethoxy)phenyl]sulphonyl}-3-(2-fluorophenyl)-5-methoxy-3-(3-piperidin-1-ylpropyl)-1,3-dihydro-2H-pyrrolo[3,2-b]pyridin-2-one;

1-[(3-chlorophenyl)sulphonyl]-3-(2-fluorophenyl)-5-methoxy-3-(3-piperidin-1-ylpropyl)-1,3-dihydro-2H-pyrrolo[3,2-b]pyridin-2-one;

3-(2-fluorophenyl)-1-[(4-isopropoxyphenyl)sulphonyl]-5-methoxy-3-(4-piperazin-1-ylbutyl)-1,3-dihydro-2H-pyrrolo[3,2-b]pyridin-2-one;

3-(2-fluorophenyl)-1-[(4-isopropoxyphenyl)sulphonyl]-5-methoxy-3-[3-(4-methylpiperazin-1-yl)propyl]-1,3-dihydro-2H-pyrrolo[3,2-b]pyridin-2-one;

3-(2-fluorophenyl)-1-[(4-isopropoxyphenyl)sulphonyl]-5-methoxy-3-[4-(4-methylpiperazin-1-yl)butyl]-1,3-dihydro-2H-pyrrolo[3,2-b]pyridin-2-one;

3-(2-fluorophenyl)-1-[(4-isopropoxyphenyl)sulphonyl]-5-methoxy-3-(3-piperidin-4-ylpropyl)-1,3-dihydro-2H-pyrrolo[3,2-b]pyridin-2-one;

3-(2-fluorophenyl)-1-[(4-isopropoxyphenyl)sulphonyl]-5-methoxy-3-(4-piperazin-1-ylbutyl)-1,3-dihydro-2H-pyrrolo[3,2-b]pyridin-2-one;

3-(2-fluorophenyl)-1-[(4-isopropoxyphenyl)sulphonyl]-5-methyl-3-(3-piperazin-1-ylpropyl)-1,3-dihydro-2H-pyrrolo[3,2-b]pyridin-2-one;

3-(2-fluorophenyl)-5-methoxy-1-[(4-methoxy-3-methylphenyl)sulphonyl]-3-(4-piperazin-1-ylbutyl)-1,3-dihydro-2H-pyrrolo[3,2-b]pyridin-2-one;

1-[(2,4-dimethoxyphenyl)sulphonyl]-3-(2-fluorophenyl)-5-methyl-3-(3-piperazin-1-ylpropyl)-1,3-dihydro-2H-pyrrolo[3,2-b]pyridin-2-one;

3-(2-fluorophenyl)-5-methoxy-1-[(4-methoxy-3-methylphenyl)sulphonyl]-3-(3-piperazin-1-ylpropyl)-1,3-dihydro-2H-pyrrolo[3,2-b]pyridin-2-one;

1-[(2,4-dimethoxyphenyl)sulphonyl]-3-(2-fluorophenyl)-5-methoxy-3-(3-piperazin-1-ylpropyl)-1,3-dihydro-2H-pyrrolo[3,2-b]pyridin-2-one;

3-(2-fluorophenyl)-1-[(4-methoxy-3-methylphenyl)sulphonyl]-5-methyl-3-(3-piperazin-1-ylpropyl)-1,3-dihydro-2H-pyrrolo[3,2-b]pyridin-2-one;

1-[(2,4-dimethoxyphenyl)sulphonyl]-3-(2-fluorophenyl)-5-methoxy-3-(4-piperazin-1-ylbutyl)-1,3-dihydro-2H-pyrrolo[3,2-b]pyridin-2-one;

3-(2-fluorophenyl)-1-[(4-isopropoxyphenyl)sulphonyl]-5-methyl-3-[3-(4-methylpiperazin-1-yl)propyl]-1,3-dihydro-2H-pyrrolo[3,2-b]pyridin-2-one;

3-(2-fluorophenyl)-5-methoxy-1-[(4-methoxy-3-methylphenyl)sulphonyl]-3-[4-(4-methylpiperazin-1-yl)butyl]-1,3-dihydro-2H-pyrrolo[3,2-b]pyridin-2-one;

in the form of a base or of addition salts with acids, in the form of pure enantiomers or of a racemic mixture.

In the text which follows, the expression protecting group Pg is understood to mean a group which makes it possible, on the one hand, to protect a reactive functional group such as a hydroxyl or an amine during synthesis and, on the other hand, to regenerate the intact reactive functional group at the end of the synthesis. Examples of protecting groups and methods of protection and deprotection are given in "Protective Group in Organic Synthesis", Green et al., 4$^{th}$ Edition, John Wiley & Sons, Inc., New York, 2007.

The expression leaving group, in the text that follows, is understood to mean a group which can be easily cleaved from a molecule by breaking a heterolytic bond, with departure of an electron pair. This group can thus be easily replaced by another group during a substitution reaction, for example. Such leaving groups are, for example, halogens or an activated hydroxyl group such as a methanesulphonate, benzenesulphonate, p-toluenesulphonate, triflate, acetate, and the like. Examples of leaving groups and references for their preparation are given in "Advanced Organic Chemistry", M. B. Smith and J. March, 6th Edition, Wiley Interscience, 2007, p. 496-501.

In accordance with the invention, it is possible to prepare the compounds of formula (I) according to a method which is characterized in that:

A compound of formula:

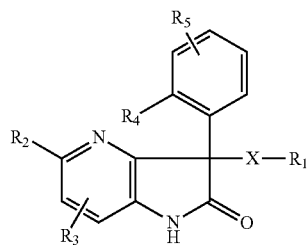

(II)

in which X, $R_1$, $R_2$, $R_3$, $R_4$ and $R_5$ are as defined for a compound of formula (I), is reacted, in the presence of a base, with a sulphonyl halide of formula:

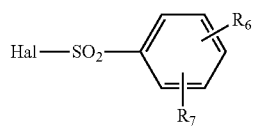

(III)

in which $R_6$ and $R_7$ are as defined for a compound of formula (I) and Hal represents a halogen atom.

Optionally, the compound of formula (I) is converted to one of its salts with inorganic or organic acids.

The reaction is carried out in the presence of a strong base such as, for example, a metal hydride such as sodium hydride or a metal alcoholate such as potassium tert-butoxide, in an anhydrous solvent such as N,N-dimethylformamide or tetrahydrofuran and at a temperature between −70° C. and +60° C. The reaction is preferably carried out using a compound of formula (III) in which Hal=Cl.

The compounds of formula (I) thus obtained may be subsequently separated from the reaction medium and purified according to conventional methods, for example by crystallization or chromatography.

The compounds of formula (I) thus obtained are isolated in the form of a free base or a salt, according to conventional techniques.

The compounds of formula (II) are prepared by reacting a compound 1,3-dihydro-2H-pyrrolo[3,2-b]pyridin-2-one of formula:

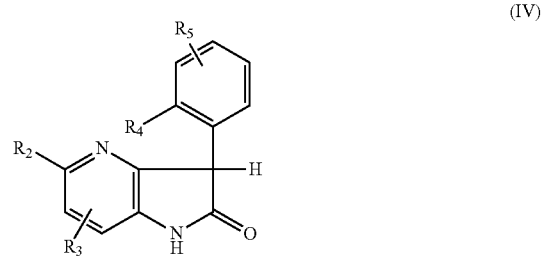

(IV)

in which $R_2$, $R_3$, $R_4$ and $R_5$ are as defined for a compound of formula (I), with a compound of formula:

Z—X—$R_1$ (V)

in which X and $R_1$ are as defined for a compound of formula (I) and Z represents a leaving group such as a halogen atom, preferably iodine or bromine, or a methanesulphonate or p-toluenesulphonate group.

The reaction is carried out in the presence of a strong base such as, for example, an alkali metal alcoholate such as potassium tert-butoxide in a solvent such as tetrahydrofuran or N,N-dimethylformamide and at a temperature between −50° C. and room temperature.

It is also possible to prepare the compounds of formula (II) by reacting a compound of formula:

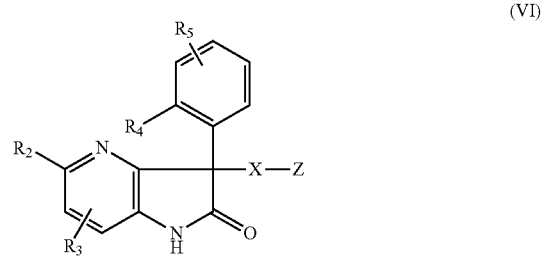

(VI)

in which X, $R_2$, $R_3$, $R_4$ and $R_5$ are as defined for a compound of formula (I) and Z represents a leaving group as described above, with a compound of formula $R_1$H (VII). The reaction is carried out in the presence of an alkali metal carbonate such as, for example, sodium carbonate and in the presence of an alkali metal halide such as, for example, sodium iodide, in a solvent such as acetonitrile or N,N-dimethylformamide and at a temperature between room temperature and the reflux temperature of the solvent.

The compounds of formula (III) are commerically available, known or prepared by known methods such as those described in EP 0 469 984 B and WO 95/18 105. For example, the compounds of formula (III) may be prepared by halogenation of the corresponding benzenesulphonic acids or their salts, for example their sodium or potassium salts. The reaction is carried out in the presence of a halogenating agent such as phosphorus oxychloride, thionyl chloride, phosphorus trichloride, phosphorus tribromide or phosphorus pentachloride, with no solvent or in a solvent such as a halogenated hydrocarbon or N,N-dimethylformamide and at a temperature between −10° C. and 200° C.

It is also possible to prepare the compounds of formula (III) by reacting chlorosulphonic acid with a compound of formula:

(VIII)

in which $R_6$ and $R_7$ are as defined for a compound of formula (I). The reaction is carried out according to the procedures described in Chlorosulphonic Acid; R. J. Cremlyn; The Royal Society of Chemistry, 2002.

The compounds of formula (IV) are known and are prepared according to known methods such as those described in WO 95/18 105 or in WO 01/55 130.

It is also possible to prepare the compounds of formula (IV) according to SCHEME 1 below in which R represents a $(C_1-C_4)$alkyl.

SCHEME 1

According to SCHEME 1, the compounds of formula (IV) are obtained by cyclization of the amine of formula (X) generated in situ by reducing the nitro group of the compounds of formula (IX). The reaction is carried out in the presence of a metal such as, for example, tin or iron, in acidic medium such as acetic acid, in a solvent such as methanol and at a temperature between room temperature and 100° C.

The compounds of formula (V) are commercially available or prepared according to known methods.

The compounds of formula (VI) are prepared by reacting a compound of formula:

(IV)

in which $R_2$, $R_3$, $R_4$ and $R_5$ are as defined for a compound of formula (I) with a compound of formula:

$$Hal-X-Z \quad (XI)$$

in which X is as defined for a compound of formula (I), Z is as defined above and Hal represents a halogen atom.

The reaction is carried out in the presence of a strong base such as, for example, an alkali metal alcoholate such as potassium tert-butoxide in a solvent such as tetrahydrofuran or N,N-dimethylformamide and at a temperature between −50° C. and room temperature.

The compounds of formula (VI) are also prepared by cyclization of a compound of formula:

(XII)

in which $R_2$, $R_3$, $R_4$, $R_5$, X and Z are as defined for a compound of formula (I).

The reaction is carried out in the presence of a metal such as, for example, tin or iron, in an acidic medium such as acetic acid, in a solvent such as methanol and at a temperature between room temperature and 100° C.

The compounds of formula (VII) are commercially available, known or prepared according to methods known to a person skilled in the art.

The compounds of formula (VIII) are known or prepared according to known methods.

The compounds of formula (IX) are prepared by reacting compounds of formula:

(XIII)

in which $R_2$ and $R_3$ are as defined for a compound of formula (I) and Hal represents a halogen atom, with a compound of formula:

(XIV)

in which $R_4$ and $R_5$ are as defined for a compound of formula (I).

The reaction is carried out in the presence of a strong base such as, for example, an alkali metal alcoholate such as potassium tert-butoxide or such as a metal hydride such as sodium hydride, in an anhydrous solvent such as N,N-dimethylformamide and at a temperature between −50° C. and room temperature.

The compounds of formula (XI), (XIII) and (XIV) are prepared according to methods well known to a person skilled in the art.

The compounds of formula (XII) are prepared by reacting a compound of formula:

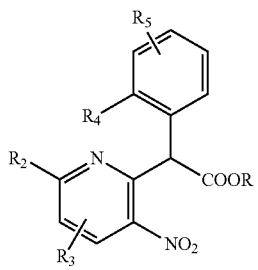

(IX)

in which $R_2$, $R_3$, $R_4$ and $R_5$ are as defined for a compound of formula (I) and R is a $C_1$-$C_4$ alkyl group, with a compound of formula:

Hal—X—Z         (XI)

in which X is as defined for a compound of formula (I), Z is as defined above and Hal represents a halogen atom.

The reaction is carried out in the presence of a strong base such as an alkali metal alcoholate such as potassium tert-butoxide in a solvent such as tetrahydrofuran or N,N-dimethylformamide and at a temperature between −50° C. and room temperature.

The N-oxides of the compounds containing an amine or a nitrogen atom are prepared according to methods known to a person skilled in the art by reacting the amine with organic peracids such as peracetic acid, trifluoroperacetic acid, performic acid, perbenzoic acid or its derivatives such as 3-chloroperbenzoic acid, at temperatures between 0° C. and 90° C., preferably at temperatures below 50° C.

In order to obtain the compounds of formula (I) in the form of optically pure isomers, it is possible to use conventional separation techniques: for example fractional recrystallizations of a salt formed from a racemic base with an optically active acid, the principle of which is well known, or conventional preparative liquid chromatography or chiral phase supercritical fluid chromatography techniques.

It is also possible to prepare the optically pure compounds of formula (I) from an optically pure intermediate compound useful for the preparation of the compounds of formula (I) according to the techniques described in WO 03/008 407.

The following EXAMPLES describe the preparation of some compounds in accordance with the invention. These examples are not limiting and merely illustrate the present invention. The numbers for the exemplified compounds refer to those given in the TABLES (I, II and III) below, which illustrate the chemical structures and the physical properties of a few compounds according to the invention.

In the Preparations and in the Examples, the following abbreviations are used:
EtOH: ethanol
ether: diethyl ether
iso ether: diisopropyl ether
DMSO: dimethyl sulphoxide
DMF: N,N-dimethylformamide
THF: tetrahydrofuran
DCM: dichloromethane
AcOEt: ethyl acetate
methanol: MeOH
2N hydrochloric ether: 2N solution of hydrochloric acid in diethyl ether
m.p.: melting point
RT: room temperature
HPLC: high-performance liquid chromatography
silica H: silica 60H gel marketed by Merck (DARMSTAD)
buffer solution pH=2: solution of 16.66 g of $KHSO_4$ and 32.32 g of $K_2SO_4$ in 1 litre of water.

The proton nuclear magnetic resonance spectra ($^1$H NMR) are recorded in DMSO-$d_6$. The chemical shifts δ are expressed in parts per million (ppm). For the interpretation of the spectra, the following abbreviations are used: s: singlet, d: doublet, t: triplet, q: quadruplet, mt: multiplet, bs: broad singlet, dd: doublet of doublet.

The optical rotations are measured on a PERKIN-ELMER 241 polarimeter.

The solvent mixtures are quantified in volume ratios.

The compounds according to the invention are analysed by LC/UV/MS (liquid chromatography/UV detection/mass spectrometry) coupling. The molecular peak (MN$^+$) and the retention time (tr) in minutes are measured.

System 1 at pH3: Method 1 (M1)
Apparatus (Agilent): HPLC chain: series 1100;
Mass spectrometer: MSD SL (Agilent)
Software: Chemstation version B.01.03 from Agilent LC/UV
Column: Symmetry C18 3.5 μm (2.1×50 mm) (Waters)
Column temperature: 25° C.
Eluents: A: $H_2O$+0.005% TFA
    B: $CH_3CN$+0.005% TFA
Flow rate: 0.4 ml/min
Gradient:

| Time (min.) | % (v/v) A/B |
|---|---|
| 0 | 100/0 |
|  | 0/100 |
| 15 | 0/100 |

UV detection: 220 nm
Injection volume: 2 μl of a solution at 0.5 mg/ml MS
Ionization mode: electrospray positive mode ESI$^+$
Mass range: 90-1500 amu
System 2 at pH7: Method 2 (M2)
Apparatus (Agilent): HPLC chain: series 1100;
Mass spectrometer: MSD SL (Agilent)
Software: Chemstation version B.01.03 from Agilent LC/UV
Column: X Terra C18 3.5 μm (2.1×50 mm) (Waters)
Column temperature: 30° C.
Eluents: A: 10 mM ammonium acetate buffer pH7
    B: $CH_3CN$
Flow rate: 0.4 ml/min Gradient:

| Time (min.) | % (v/v) A/B |
| --- | --- |
| 0 | 100/0 |
| 10 | 10/90 |
| 15 | 10/90 |

UV detection: 220 nm
Injection volume: 2 μl of a solution at 0.5 mg/ml MS
Ionization mode: electrospray positive mode ESI$^+$
Mass range: 90-1500 amu
System 3 at pH2.2: Method 3 (M3)
Apparatus (Waters): HPLC chain: Alliance 2695;
UV detector: PDA 996
Mass spectrometer: Platform LCZ (Micromass)
Software: MassLynx version 4.0 from Waters-Micromass LC/UV
Column: Symmetry C18 3.5 μm (2.1×50 mm) (Waters)
Column temperature: 40° C.
Eluents: A: H$_2$O+0.05% TFA
B: CH$_3$CN+0.035% TFA
Flow rate: 0.5 ml/min
Gradient:

| Time (min.) | % (v/v) A/B |
| --- | --- |
| 0.0 | 100/0 |
| 6.0 | 0/100 |
| 7.0 | 0/100 |
| 7.1 | 100/0 |
| 10.0 | 100/0 |

UV detection: 220 nm
Injection volume: 2 μl of a solution at 0.5 mg/ml MS
Ionization mode: electrospray positive mode ESI$^+$
Mass range: 120-1500 amu
System 4 at pH3: Method 4 (M4)
Apparatus (Agilent): HPLC chain: series 1100;
Mass spectrometer: MSD SL (Agilent)
Software: Chemstation version B.01.03 from Agilent LC/UV
Column: Symmetry C18 3.5 μm (2.1×50 mm) (Waters)
Column temperature: 25° C.
Eluents: A: H$_2$O+0.005% TFA
B: CH$_3$CN+0.005% TFA
Flow rate: 0.4 ml/min
Gradient:

| Time (min.) | % (v/v) A/B |
| --- | --- |
| 0 | 100/0 |
| 10 | 0/100 |
| 15 | 0/100 |

UV detection: 220 nm
Injection volume: 2 μl of a solution at 0.5 mg/ml MS
Ionization mode: electrospray positive mode ESI$^+$
Mass range: 90-1500 amu

PREPARATIONS

1. Preparation of the compounds of formula (IX).
Preparation 1.1
Methyl (2-fluorophenyl)(6-methoxy-3-nitropyridin-2-yl) acetate.

$R_2$=OMe; $R_3$=H; $R_4$=F; $R_5$=H; R=Me    (IX)

To 12.7 g of sodium hydride at 60% in oil in suspension in 600 ml of DMF is added at 0° C., dropwise, the mixture of 20 g of 2-chloro-6-methoxy-3-nitropyridine and 20.6 g of methyl 2-fluorophenyl acetate in solution in 100 ml of DMF. The reaction mixture is stirred for 3 h, allowing the temperature to rise to RT. 500 ml of a 5% aqueous NaHCO$_3$ solution are added and the mixture is extracted with 250 ml of AcOEt. The organic phase is washed with 300 ml of a 5% aqueous NaHCO$_3$ solution, it is dried over Na$_2$SO$_4$, and then the solvents are evaporated under reduced pressure. The residue is purified by silica gel chromatography, eluting with a cyclohexane/ethyl acetate mixture to give the expected compound in the form of a liquid.

2. Preparation of the compounds of formula (IV).
Preparation 2.1
3-(2-Fluorophenyl)-5-methoxy-1,3-dihydro-2H-pyrrolo[3,2-b]pyridin-2-one.

$R_2$=OMe; $R_3$=H; $R_4$=F; $R_5$=H.    (IV)

To 37 g of the compound prepared during the preparation 1.1 in 530 ml of EtOH is added 29 g of iron and then 42 ml of acetic acid. The reaction mixture is stirred under reflux for 5 h. The solvents are partially evaporated under reduced pressure and then 250 ml of a 5% aqueous NaHCO$_3$ solution and 300 ml of AcOEt are added. After stirring, the mixture is filtered. After separation of the filtrate by decantation, the organic phase is washed with 100 ml of a 5% aqueous NaHCO$_3$ solution, dried over Na$_2$SO$_4$ and concentrated under reduced pressure. The solid residue obtained is taken up in iso ether, filtered and dried at 50° C. under vacuum.
MH$^+$=259; tr=6.60 min (M1)

3. Preparation of the compounds of formula (VI).
Preparation 3.1.
3-(3-Chloropropyl)-3-(2-fluorophenyl)-5-methoxy-1,3-dihydro-2H-pyrrolo[3,2-b]pyridin-2-one, dextrorotatory isomer and laevorotatory isomer $R_2$=OMe; $R_3$=H; $R_4$=F; $R_5$=H; X=—(CH$_2$)$_3$—;
Z=Cl    (VI)

A) Methyl 5-chloro-2-(2-fluorophenyl)-2-(6-methoxy-3-nitropyridin-2-yl) pentanoate (XII)

To 9.3 g of sodium hydride at 60% in oil in suspension in 900 ml of DMF is added at 0° C., dropwise, the mixture of 20 g of 2-chloro-6-methoxy-3-nitropyridine and 19.6 g of methyl 2-fluorophenyl acetate in solution in 100 ml of DMF. The reaction mixture is stirred for 3 h, allowing the temperature to rise to RT, and then 34 ml of 1-chloro-3-iodopropane are added. The mixture is stirred at RT for 48 h. 500 ml of a 5% aqueous NaHCO$_3$ solution are added and the mixture is extracted with 500 ml of AcOEt. The organic phase is washed with 300 ml of a 5% aqueous NaHCO$_3$ solution, it is dried over Na$_2$SO$_4$ and then the solvents are evaporated under reduced pressure. The residue is purified by silica gel chromatography, eluting with a cyclohexane/ethyl acetate mixture to give the expected compound in liquid form which is used as it is in the next step.

B) 3-(3-Chloropropyl)-3-(2-fluorophenyl)-5-methoxy-1,3-dihydro-2H-pyrrolo[3,2-b]pyridin-2-one, dextrorotatory isomer and laevorotatory isomer To 42 g of the compound of the preceding step in 530 ml of EtOH is added 29.6 g of iron and then 43 ml of acetic acid. The reaction mixture is stirred under reflux for 5 h. The solvents are partially evaporated under reduced pressure and then 250 ml of a 5% aqueous NaHCO$_3$ solution and 500 ml of AcOEt are added. After stirring, the reaction mixture is filtered. After separating the filtrate by decantation, the organic phase is washed with 100 ml of a 5% aqueous NaHCO$_3$ solution, dried over Na$_2$SO$_4$ and concentrated under reduced pressure. The solid residue obtained is taken up in iso ether, filtered, dried at 50° C. under vacuum.

The enantiomers of the compound thus obtained are separated by chiral phase liquid chromatography under the following conditions:

Equipment: Waters Delta Prep 4000 chromatography system;
Chiral column: CHIRALPAK AS-VCSP;
Mobile phase: acetonitrile 100%;
Flow rate: 120 ml/minute;
Pressure: 50 bar;
UV detection: 254 nm.

After separation of the enantiomers, the following are obtained:

dextrorotatory isomer in the form of a solid:

$\alpha_D^{20}=+1.2°(c=1; \text{MeOH})$;

m.p.=65° C.
the laevorotatory isomer in the form of a solid:

$\alpha_D^{20}=-1.5°(c=1; \text{MeOH})$;

m.p.=63° C.
Preparation 3.2.
3-(4-Chlorobutyl)-3-(2-fluorophenyl)-5-methoxy-1,3-dihydro-2H-pyrrolo[3,2-b]pyridin-2-one (VI), dextrorotatory isomer and laevorotatory isomer.

$R_2$=OMe; $R_3$=H; $R_4$=F; $R_5$=H; X=—(CH$_2$)$_4$—;
$Z$=Cl (VI)

A) Methyl 6-chloro-2-(2-fluorophenyl)-2-(6-methoxy-3-nitropyridin-2-yl)hexanoate (XII)

To 9.3 g of sodium hydride at 60% in oil in suspension in 900 ml of DMF is added at 0° C., dropwise, the mixture of 20 g of 2-chloro-6-methoxy-3-nitropyridine and 19.6 g of methyl 2-fluorophenyl acetate in solution in 100 ml of DMF. The reaction mixture is stirred for 3 h, allowing the temperature to rise to room temperature and then 34 ml of iodochlorobutane are added. The mixture is stirred at RT for 48 h. 500 ml of a 5% aqueous NaHCO$_3$ solution are added and the mixture is extracted with 500 ml of AcOEt. The organic phase is washed with 300 ml of a 5% aqueous NaHCO$_3$ solution, dried over Na$_2$SO$_4$ and then the solvents are then evaporated under reduced pressure. The residue is purified by silica gel chromatography, eluting with a cyclohexane/ethyl acetate mixture to give the expected compound in the form of a liquid which is used as it is in the next step.

B) 3-(4-Chlorobutyl)-3-(2-fluorophenyl)-5-methoxy-1,3-dihydro-2H-pyrrolo[3,2-b]pyridin-2-one (VI)

To 42 g of the compound of the preceding step in 530 ml of ethanol are added 29.6 g of iron and then 43 ml of acetic acid. The reaction mixture is stirred under reflux for 5 h. The solvents are partially evaporated under reduced pressure and then 250 ml of a 5% aqueous NaHCO$_3$ solution and 500 ml of AcOEt are added. After stirring, the reaction mixture is filtered. After separating the filtrate by decantation, the organic phase is washed with 100 ml of a 5% aqueous NaHCO$_3$ solution, dried over Na$_2$SO$_4$ and concentrated under reduced pressure. The solid residue obtained is taken up in iso ether, filtered, dried at 50° C. under vacuum to give the expected product in racemic form.

The enantiomers of the compound thus obtained are separated by chiral phase liquid chromatography under the following conditions:

Equipment: Waters Delta Prep 4000 chromatography system;
Chiral column: CHIRALPAK AS-VCSP;
Mobile phase: acetonitrile 100%;
Flow rate: 120 ml/minute;
Pressure: 50 bar;
UV detection: 254 nm.

After separation of the enantiomers, the following are obtained:

the dextrorotatory isomer in the form of a solid:

$\alpha_D^{20}=+13.5°$ ($c=1$; MeOH);

the laevorotatory isomer in the form of a solid:

$\alpha_D^{20}=-14.6(c=1; \text{MeOH})$;

Preparation 3.3.
3-(3-Chloropropyl)-3-(2-fluorophenyl)-5-methyl-1,3-dihydro-2H-pyrrolo[3,2-b]pyridin-2-one.

$R_2$=Me; $R_3$=H; $R_4$=F; $R_5$=H; X=—(CH$_2$)$_3$—;
$Z$=Cl. (VI)

A) Methyl 5-chloro-2-(2-fluorophenyl)-2-(6-methyl-3-nitropyridin-2-yl) pentanoate (XII)

To 11.6 g of sodium hydride at 60% in oil in suspension in 100 ml of DMF is added at −10° C., dropwise, the mixture of 20 g of 2-chloro-6-methyl-3-nitropyridine and 21.5 g of methyl 2-fluorophenyl acetate in solution in 100 ml of DMF. The reaction mixture is stirred for 1 h 30 min, allowing the temperature to rise to RT; and then 19.1 ml of 1-chloro-3-iodopropane are added. The mixture is stirred at RT for 18 h. The mixture is poured over 600 ml of a 10% aqueous NH$_4$Cl solution and the mixture is extracted with 300 ml of AcOEt. The organic phase is washed with brine, dried over MgSO$_4$, filtered and then concentrated under reduced pressure. The residue is purified by silica gel chromatography, eluting with a heptane/dichloromethane mixture to give the expected compound in the form of an orange-coloured oil.

MH$^+$=381; tr=9.15 min (M4)

B) 3-(3-Chloropropyl)-3-(2-fluorophenyl)-5-methyl-1,3-dihydro-2H-pyrrolo[3,2-b]pyridin-2-one (VI)

To 13.6 g of the compound of the preceding step in solution in 120 ml of MeOH are added 6 g of iron and then 14.2 ml of acetic acid. The reaction mixture is stirred under reflux for 3 h. The mixture is concentrated under reduced pressure and then the residue is taken up in a mixture of 200 ml of AcOEt and 500 ml of 1N hydrochloric acid. The organic phase is washed with brine, dried over MgSO$_4$, filtered and concentrated under reduced pressure. The solid residue obtained is taken up in iso ether, filtered and dried at 50° C. under vacuum.

MH$^+$=319; tr=7.10 min (M4)

4. Preparations of the compounds of formula (II).

Preparation 4.1.

tert-Butyl 4-{3-[3-(2-fluorophenyl)-5-methoxy-2-oxo-2,3-dihydro-1H-pyrrolo[3,2-b]pyridin-3-yl]propyl}piperazine-1-carboxylate, single isomer.

$R_2$=OMe; $R_3$=H; $R_4$=F; $R_5$=H; (II)

X=—(CH$_2$)$_3$—; $R_1$=

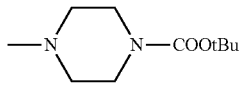

To a solution of 0.3 g of the compound of preparation 3.1 laevorotatory isomer in 5 ml of DMF are added 0.13 g of sodium iodide, 0.28 g of sodium carbonate and 0.41 g of tert-butyl piperazine-1-carboxylate. The mixture is stirred at 85° C. for 6 h. A saturated aqueous NH$_4$Cl solution is added and the mixture is extracted with AcOEt. The organic phase is washed with a saturated aqueous NaCl solution, it is dried over Na$_2$SO$_4$ and then the solvents are evaporated under reduced pressure. The residue is purified by silica gel chromatography, eluting with a dichloromethane/methanol mixture to give the expected compound in the form of an oil.

MH$^+$=485; tr=5.67 min (M1)

Preparation 4.2 tert-Butyl 4-{3-[3-(2-fluorophenyl)-5-methoxy-2-oxo-2,3-dihydro-1H-pyrrolo[3,2-b]pyridin-3-yl]propyl}piperazine-1-carboxylate, single isomer.

$R_2$=OMe; $R_3$=H; $R_4$=F; $R_5$=H; (II)

X=—(CH$_2$)$_3$—; $R_1$=

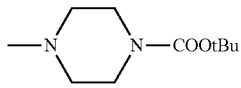

Using the same procedure described in preparation 4.1, starting with the compound of preparation 3.1 dextrorotatory isomer, the expected compound is obtained.

MH$^+$=485; tr=5.68 min (Method M1)

Preparation 4.3

3-(2-Fluorophenyl)-5-methoxy-3-(3-piperidin-1-ylpropyl)-1,3-dihydro-2H-pyrrolo[3,2-b]pyridin-2-one, single isomer.

$R_2$=OMe; $R_3$=H; $R_4$=F; $R_5$=H; (II)

X=—(CH$_2$)$_3$—; $R_1$=

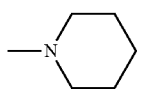

To a solution of 0.3 g of the compound of preparation 3.1 laevorotatory isomer in 5 ml of DMF are added 0.13 g of sodium iodide, 0.28 g of sodium carbonate and 0.45 g of piperidine. The mixture is stirred at 85° C. for 6 h. A saturated aqueous NH$_4$Cl solution is added and the mixture is extracted with AcOEt. The organic phase is washed with a saturated aqueous NaCl solution, it is dried over Na$_2$SO$_4$ and then the solvents are evaporated under reduced pressure. The residue is purified by silica gel chromatography, eluting with a dichloromethane/methanol mixture to give the expected compound in the form of an oil.

MH$^+$=384; tr=5.02 min (Method M1)

Preparation 4.4

3-(2-Fluorophenyl)-5-methoxy-3-(3-piperidin-1-ylpropyl)-1,3-dihydro-2H-pyrrolo[3,2-b]pyrid in-2-one, single isomer.

$R_2$=OMe; $R_3$=H; $R_4$=F; $R_5$=H; (II)

X=—(CH$_2$)$_3$—; $R_1$=

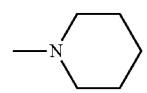

Using the same procedure described in preparation 4.3 starting with the compound of preparation 3.1 dextrorotatory isomer, the expected compound is obtained.

MH$^+$=384; tr=5.03 min (M1)

Preparation 4.5 tert-Butyl 4-{4-[3-(2-fluorophenyl)-5-methoxy-2-oxo-2,3-dihydro-1H-pyrrolo[3,2-b]pyridin-3-yl]butyl}piperazine-1-carboxylate.

$R_2$=OMe; $R_3$=H; $R_4$=F; $R_5$=H; (II)

X=—(CH$_2$)$_4$—; $R_1$=

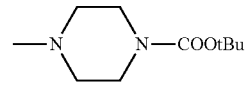

To a solution of 0.3 g of the compound of preparation 3.2 in 5 ml of DMF are added 0.13 g of sodium iodide, 0.28 g of sodium carbonate and 0.41 g of tert-butyl piperazine-1-carboxylate. The mixture is stirred at 85° C. for 6 h. A saturated aqueous NH$_4$Cl solution is added and the mixture is extracted with AcOEt. The organic phase is washed with a saturated aqueous NaCl solution, dried over Na$_2$SO$_4$, and then the solvents are evaporated under reduced pressure. The residue is purified by silica gel chromatography, eluting with a dichloromethane/methanol mixture to give the expected compound in the form of an oil.

MH$^+$=399; tr=5.29 min (M1)

Preparation 4.6 tert-Butyl 4-{3-[3-(2-fluorophenyl)-5-methyl-2-oxo-2,3-dihydro-1H-pyrrolo[3,2-b]pyridin-3-yl]propyl}piperazine-1-carboxylate.

$R_2$=Me; $R_3$=H; $R_4$=F; $R_5$=H; (II)

X=—(CH$_2$)$_3$—; $R_1$=

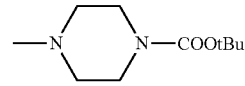

To a solution of 3.4 g of the compound of preparation 3.3 in 40 ml of DMF are added 1.6 g of sodium iodide, 1.13 g of sodium carbonate and 2.98 g of tert-butyl piperazine-1-carboxylate. The mixture is stirred at 100° C. for 3 h. 300 ml of a 10% aqueous NH₄Cl solution are added and the mixture is extracted with AcOEt. The organic phase is washed with a saturated aqueous NaCl solution, dried over MgSO₄, filtered and concentrated under reduced pressure. The residue is triturated in iso ether and the expected compound is obtained in the form of a pale orange-coloured precipitate.

MH⁺=469; tr=5.35 min (M4)

The enantiomers of the compound thus obtained are separated by chiral phase liquid chromatography under the following conditions:

Equipment: Waters Delta Prep 4000 chromatography system

Chiral column: CHIRALPAK AS-VCSP;
Mobile phase: acetonitrile 100%;
Flow rate: 120 ml/minute;
Pressure: 50 bar;
UV detection: 254 nm.

After separation of the enantiomers, the following are obtained:

the dextrorotatory isomer in the form of a resin:

$\alpha_D^{20}$=+15.1°(c=1; MeOH);

MH⁺=469; 4.82 min (M4)

the laevorotatory isomer in the form of a resin:

$\alpha_D^{20}$=−12.3° (c=1; MeOH);

MH⁺=469; 3.71 min (M3)

Preparation 4.7

3-(2-Fluorophenyl)-5-methoxy-3-[3-(4-methylpiperazin-1-yl)propyl]-1,3-dihydro-2H-pyrrolo[3,2-b]pyridin-2-one, single isomer.

R₂=OMe; R₃=H; R₄=F; R₅=H;    (II)

X=—(CH₂)₃—; R₁=

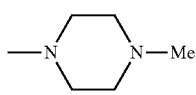

To a solution of 167 mg of the compound of preparation 3.1 dextrorotatory isomer in 2 ml of DMF are added 75 mg of sodium iodide, 53 mg of sodium carbonate and 84 μl of 1-methylpiperazine. The mixture is stirred at 100° C. for 1 h 30 min. 30 ml of a 10% aqueous NH₄Cl solution are added and the mixture is extracted with AcOEt. The organic phase is washed with a saturated aqueous NaCl solution, it is dried over MgSO₄, filtered and concentrated under reduced pressure. The residue is purified by silica gel chromatography, eluting with a dichloromethane/MeOH mixture to give the expected compound in the form of a resin.

MH⁺=399; tr=3.32 min (M3)

Preparation 4.8 tert-Butyl 4-{4-[3-(2-fluorophenyl)-5-methoxy-2-oxo-2,3-dihydro-1H-pyrrolo[3,2-b]pyridin-3-yl]butyl}piperazine-1-carboxylate, single isomer.

R₂=OMe; R₃=H; R₄=F; R₅=H;    (II)

X=—(CH₂)₃—; R₁=

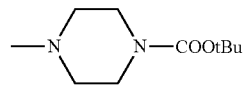

Using the same procedure described in preparation 4.5 starting with the compound of preparation 3.2 dextrorotatory isomer, the expected compound is obtained.

MH⁺=499; tr=5.32 min (M4)

Preparation 4.9 tert-Butyl 4-{3-[3-(2-fluorophenyl)-5-methoxy-2-oxo-2,3-dihydro-1H-pyrrolo[3,2-b]pyridin-3-yl]propyl}piperidine-1-carboxylate.

R₂=OMe; R₃=H; R₄=F; R₅=H;    (II)

X=—(CH₂)₃—; R₁=

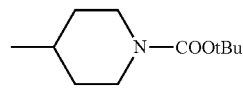

To a solution of 0.6 g of the compound obtained in preparation 2.1 in 20 ml of DMF are added, at −40° C., 0.66 g of tBuOK, and then after 15 min, 0.91 g of tert-butyl 4-(3-iodopropyl)piperidine-1-carboxylate. The mixture is stirred for 4 h after returning to −20° C., and then diluted with 150 ml of AcOEt and 300 ml of a 10% aqueous NH₄Cl solution; the organic phase is washed with a saturated NaCl solution, dried over MgSO₄, filtered and concentrated under reduced pressure. The residue is purified by silica gel chromatography, eluting with a heptane/AcOEt mixture, and then with a dichloromethane/MeOH mixture to give the expected compound in the form of a resin.

MH⁺=484; tr=9.51 min (M4)

Example 1

Compound No. 1

3-(2-Fluorophenyl)-1-[(4-isopropoxyphenyl)sulphonyl]-5-methoxy-3-(3-piperazin-1-ylpropyl)-1,3-dihydro-2H-pyrrolo[3,2-b]pyridin-2-one hydrochloride, single isomer To a solution of 0.48 g of the compound of preparation 4.1 in 8 ml of THF is added, at 0° C., 0.13 g of potassium tert-butoxide. After stirring for 15 minutes at 0° C., 0.12 g of 4-isopropoxybenzenesulphonyl chloride is added. After stirring for 6 hours at 20° C., the mixture is hydrolysed with a saturated ammonium chloride solution and then extracted with AcOEt. The organic phase is washed with water, dried over MgSO₄, filtered and then evaporated to dryness, purified by silica gel chromatography, eluting with a dichloromethane/methanol mixture. The product is then stirred in a 2N hydrochloric ether solution and is then filtered to give the desired compound in the form of a white powder.

m.p.=123° C.

MH⁺=583; tr=6.42 min (Method M1)

Example 2

Compound No. 3

3-(2-Fluorophenyl)-5-methoxy-1-[(3-methoxyphenyl)sulphonyl]-3-(3-piperazin-1-ylpropyl)-1,3-dihydro-2H-pyrrolo[3,2-b]pyridin-2-one hydrochloride, single isomer Using the same procedure described in Example 1, starting with the compound of preparation 4.2 single isomer and 3-methoxybenzenesulphonyl chloride, the expected compound is obtained.
m.p.=178° C.
$MH^+$=555; tr=5.49 nm (Method M1)

Example 3

Compound No. 5

3-(2-Fluorophenyl)-1-[(4-isopropoxyphenyl)sulphonyl]-5-methoxy-3-(3-piperidin-1-ylpropyl)-1,3-dihydro-2H-pyrrolo[3,2-b]pyridin-2-one hydrochloride, single isomer Using the same procedure described in Example 1, starting with the compound of preparation 4.3 single isomer and 4-isopropoxybenzenesulphonyl chloride, the expected compound is obtained.
m.p.=156° C.
$MH^+$=582; tr=6.57 min (Method M1)

Example 4

Compound No. 7

3-(2-Fluorophenyl)-5-methoxy-1-[(3-methoxyphenyl)sulphonyl]-3-(3-piperidin-1-ylpropyl)-1,3-dihydro-2H-pyrrolo[3,2-b]pyridin-2-one hydrochloride, single isomer Using the same procedure described in Example 1, starting with the compound of preparation 4.4 single isomer and 3-methoxybenzenesulphonyl chloride, the expected compound is obtained.
m.p.=148° C.
$MH^+$=554; tr=6.59 min (Method M1)

Example 5

Compound No. 10

3-(2-Fluorophenyl)-1-[(4-isopropoxyphenyl)sulphonyl]-5-methoxy-3-(4-piperazin-1-ylbutyl)-1,3-dihydro-2H-pyrrolo[3,2-b]pyridin-2-one, racemic mixture To a solution of 0.48 g of the racemic compound of preparation 4.5 in 8 ml of THF is added, at 0° C., 0.13 g of potassium tert-butoxide. After stirring for 15 minutes at 0° C., 0.12 g of 4-isopropoxybenzenesulphonyl chloride is added. After stirring for 6 hours at 20° C., the mixture is hydrolysed with a saturated $NH_4Cl$ solution and then extracted with AcOEt. The organic phase is washed with water, dried over $MgSO_4$, filtered and then evaporated to dryness, purified by silica gel chromatography, eluting with a dichloromethane/methanol mixture. The product is then stirred in a 2N hydrochloric ether solution and is then filtered to give the desired compound in the form of a white powder.
m.p.=210° C.
$MH^+$=597; tr=6.26 min (Method M1)

Example 6

Compound No. 21

3-(2-Fluorophenyl)-5-methoxy-1-[(4-methoxy-3-methylphenyl)sulphonyl]-3-[4-(4-methylpiperazin-1-yl)butyl]-1,3-dihydro-2H-pyrrolo[3,2-b]pyridin-2-one, single isomer To a solution of 185 mg of Compound No. 17 in 1 ml of methanol and 2 ml of DCM are added at 0° C. 60 µl of a 37% aqueous formaldehyde solution, 20 µl of AcOH, and then after 10 min 179 mg of $NaBH(OAc)_3$. The mixture is stirred for 18 hours with a return to RT, diluted with 30 ml of AcOEt and 20 ml of a 10% aqueous $NaHCO_3$ solution. The organic phase is washed with a saturated aqueous NaCl solution, dried over $MgSO_4$, filtered and then evaporated to dryness. The residue is purified by silica gel chromatography, eluting with a dichloromethane/methanol mixture supplemented with 0.2% aqueous ammonia at 20%, to give the expected compound in the form of a white resin.
$MH^+$=597; tr=5.91 min (M4)

Example 7

Compound No. 15

3-(2-Fluorophenyl)-1-[(4-isopropoxyphenyl)sulphonyl]-5-methyl-3-(3-piperazin-1-ylpropyl)-1,3-dihydro-2H-pyrrolo[3,2-b]pyridin-2-one hydrochloride, single isomer By using the method described in Example 1, starting with the dextrorotatory isomer obtained in preparation 4.6, the desired compound is obtained in the form of a white powder.
m.p.=150° C.
$MH^+$=567; tr=5.73 min (M4)

The tables which follow illustrate the chemical structures and the physical properties of a few examples of compounds according to the invention, obtained according to the procedures described in the examples above.

In these tables:

Me, Et and iPr represent respectively methyl, ethyl and isopropyl groups.

TABLE I

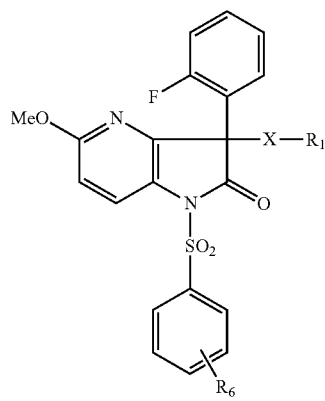

R₂ = OMe
R₃ = H
R₄ = F
R₅ = H
R₇ = H

| Compound No. | X | R¹ | R⁶ | Salts/base $\alpha_D^{20}$ (c; solvent) | m.p. °C. MH⁺; tr (conditions) |
|---|---|---|---|---|---|
| 1 | —(CH₂)₃— | —N(piperazinyl)NH | 4-OiPr | HCl −32.8 (5 mg/ml; EtOAc) | 131° C. 583.2; 6.42 (M1) |
| 2 | —(CH₂)₃— | —N(piperazinyl)NH | 4-OiPr | HCl +30.4 (5.2 mg/ml; EtOAc) | 123° C. 583.2; 6.42 (M1) |
| 3 | —(CH₂)₃— | —N(piperazinyl)NH | 3-OMe | HCl +21.4 (5.7 mg/ml; EtOAc) | 178° C. 555.4; 5.49 (M1) |
| 4 | —(CH₂)₃— | —N(piperazinyl)NH | 3-Cl | HCl +34.1 (5.7 mg/ml; EtOAc) | 177° C. 559.2; 6.24 (M1) |
| 5 | —(CH₂)₃— | —N(piperidinyl) | 4-OiPr | HCl −36.4 (5.0 mg/ml; EtOAc) | 119° C.; 582.4; 6.57 (M1) |
| 6 | —(CH₂)₃— | —N(piperidinyl) | 4-OiPr | HCl +38.1 (5.2 mg/ml; EtOAc) | 157° C. 582.4; 6.57 (M1) |
| 7 | —(CH₂)₃— | —N(piperidinyl) | 3-OMe | HCl +45.2 (5.9 mg/ml; EtOAc) | 148° C. 554.1; 6.59 (M1) |
| 8 | —(CH₂)₃— | —N(piperidinyl) | 4-OCHF₂ | HCl +44.2 (5.2 mg/ml; EtOAc) | 133° C. 590.4; 6.27 (M1) |
| 9 | —(CH₂)₃— | —N(piperidinyl) | 3-Cl | HCl +44.3 (5.1 mg/ml; EtOAc) | 148° C. 558.2; 6.81 (M1) |
| 10 | —(CH₂)₄— | —N(piperazinyl)NH | 4-OiPr | HCl (+/−) | 210° C. 597.0; 6.26 (M1) |

TABLE I-continued

| | | | | | |
|---|---|---|---|---|---|
| 11 | —(CH$_2$)$_3$— | —N⌒N—Me (piperazine) | 4-OiPr | HCl +14 (0.5; MeOH) | 190° C. 597; 6.24 (M4) |
| 12 | —(CH$_2$)$_4$— | —N⌒N—Me (piperazine) | 4-OiPr | +49.2 (0.51; AcOEt) | 52° C. 611; 6.14 (M4) |
| 13 | —(CH$_2$)$_3$— | 4-methylpiperidine (NH) | 4-OiPr | HCl +14.5 (0.5; MeOH) | 582; 7.01 (M4) |
| 14 | —(CH$_2$)$_4$— | —N⌒NH (piperazine) | 4-OiPr | HCl +10.5 (0.5; MeOH) | 133° C. 597; 5.78 (M4) |

TABLE II (I)

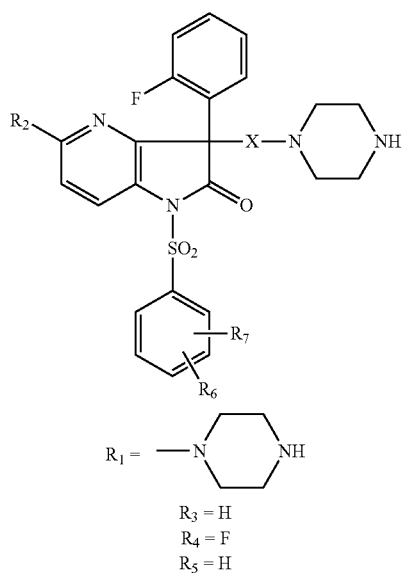

$R_1 = $ —N⌒NH $R_3 = H$
$R_4 = F$
$R_5 = H$

| Compound No. | X | R$_2$ | R$_6$ | R$_7$ | Salts/base α$_D^{20}$ (c; solvent) | m.p. °C. MH$^+$; tr (conditions) |
|---|---|---|---|---|---|---|
| 15 | —(CH$_2$)$_3$— | Me | 4-OiPr | H | HCl +16.8 (0.5; MeOH) | 150° C. 567; 5.73 (M4) |
| 17 | —(CH$_2$)$_4$— | OMe | 4-OMe | 3-Me | HCl +35.7 (0.51; MeOH) | 158° C. 583; 5.58 (M4) |
| 18 | —(CH$_2$)$_3$— | Me | 4-OMe | 2-OMe | HCl +47 (0.5; MeOH) | 176° C. 569; 5.16 (M4) |
| 19 | —(CH$_2$)$_3$— | OMe | 4-OMe | 3-Me | HCl +47.2 (0.5; MeOH) | 160° C. 569; 6.13 (M4) |
| 20 | —(CH$_2$)$_3$— | OMe | 4-OMe | 2-OMe | HCl +35.4 (0,5; MeOH) | 170° C. 858; 5.85 (M4) |
| 22 | —(CH$_2$)$_3$— | Me | 4-OMe | 3-Me | HCl +56.7 (0.51; MeOH) | 162° C. 553; 5.51 (M4) |
| 23 | —(CH$_2$)$_4$— | OMe | 4-OMe | 2-OMe | HCl +35.8 (0.52; MeOH) | 170° C. 599; 5.25 (M4) |

TABLE III (I)

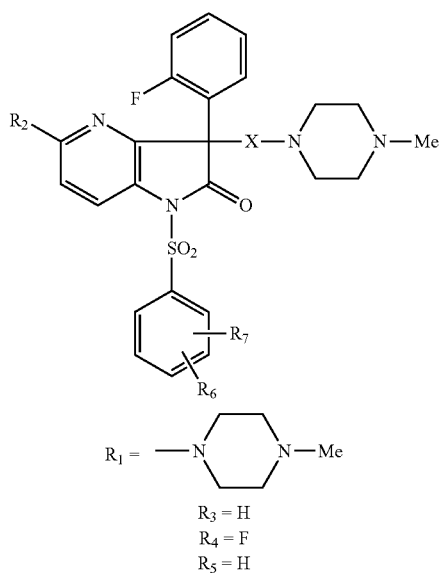

$R_1 = $ —N⌒N—Me $R_3 = H$
$R_4 = F$
$R_5 = H$

| Compound No. | X | R$_2$ | R$_6$ | R$_7$ | Salts/base α$_D^{20}$ (c; solvent) | m.p. °C. MH$^+$; tr (conditions) |
|---|---|---|---|---|---|---|
| 16 | —(CH$_2$)$_3$— | Me | 4-OiPr | H | HCl +16.9 (0.5; MeOH) | 218° C. 581; 5.96 (M4) |
| 21 | —(CH$_2$)$_4$— | OMe | 4-OMe | 3-Me | — +36.5 (0.49; AcOEt) | 55° C. 597; 5.91 (M4) |

The compounds according to the invention were the subject of pharmacological trials.

The affinity of the compounds of formula (I) according to the invention for the arginine-vasopressin V$_{1a}$ receptors was determined in vitro using the method described by M. Thibonnier et al., J. Biol. Chem., 1994, 269, 3304-3310. This method consisted in studying in vitro the displacement of tritiated arginine-vasopressin ([3H]-AVP) at the V$_{1a}$ receptors present on membrane or cell preparations carrying the rat or human V$_{1a}$ receptors. The compounds of formula (I) exhibit affinity for the human V$_{1a}$ receptors for arginine-vasopressin with IC$_{50}$ (concentration inhibiting by 50% the binding of tritiated arginine-vasopressin ([3H]-AVP to its receptors) values generally less than 10 nanomolar ($10^{-8}$ M) in the latter test.

The affinity of the compounds of formula (I) according to the invention for the arginine-vasopressin $V_{1b}$ receptors was determined in vitro using the method described by Y. de Keyser et al. in Febs Letters, 1994, 356, 215-220. This method consists in studying in vitro the displacement of tritiated arginine-vasopressin ([3H]-AVP) at the $V_{1b}$ receptors present on cell preparations carrying the human $V_{1b}$ receptors. Some compounds studied further exhibit affinity for the human $V_{1b}$ receptors with $IC_{50}$ values of less than 30 nanomolar ($3.10^{-8}$ M) in the latter test.

Th affinity of the compounds of formula (I) according to the invention for the vasopressin $V_2$ receptors was also studied (method described by M. Birnbaumer et al. in Nature (Lond.), 1992, 357, 333-335). The compounds studied have little or no affinity for the human $V_2$ receptors with $IC_{50}$ values greater than $10^{-7}$ M.

The affinity of the compounds according to the invention for the oxytocin receptors was determined in an in vitro binding test using the method described by J. Elands et al. in Eur. J. Pharmacol., 1987, 147, 197-207. This method consists in studying in vitro the displacement of a radioiodinated analogue of oxytocin at the oxytocin receptors in a membrane preparation of cells transfected with the human uterine oxytocin receptor.

The compounds studied have little or no affinity for the human oxytocin receptors with $IC_{50}$ values generally greater than $10^{-7}$ M.

TABLE IV which follows illustrates the comparative pharmacological results for the compounds No. 2, No. 4 and No. 11 according to the invention with the prior art compounds α and β in the various in-vitro tests measuring the affinity at the human $V_{1a}$, $V_{1b}$, $V_2$ and oxytocin receptors. The results are expressed by the 50% inhibitory concentration ($IC_{50}$) in nanomolar (nM).

TABLE IV

| Compound No: | $IC_{50} V_{1a}$ (nM) | $IC_{50} V_{1b}$ (nM) | $IC_{50} V_2$ (nM) | $IC_{50}$ OT (nM) |
|---|---|---|---|---|
| 2 | 0.82 | 350 | 120 | 71 |
| 4 | 8.9 | >1000 | >1000 | >1000 |
| 11 | 7.1 | >1000 | 210 | 100 |
| Compound α | 23 | 210 | 19 | 100 |
| Compound β | 18 | 180 | 13 | 69 |

The agonist or antagonist character of the compounds is determined in vitro in a test for measuring intracellular calcium (FLIPR) on cells expressing the human V1a receptors according to the general technique described in Sullivan et al, Methods Mol. Biol., 1999, 114, 125-133, using 1 µM Fluo-4 AM and in an AVP-induced platelet aggregation test on human PRP (platelet rich plasma) according to the methodology described in J. Clin. Invest., 1993, 92, 224.231. The compounds are preincubated for 30 minutes before the addition of arginine vasopressin in order to determine the agonist and antagonist properties of these molecules. The $IC_{50}$ values of the compounds according to the invention for the $V_{1a}$ receptors measured in these studies are low (less than $2\times10^{-8}$ M).

These pharmacological results show that the compounds according to the invention, in particular the compounds No. 2 and No. 4 are $V_{1a}$ receptor antagonists by blocking the pharmacological effects caused by arginine-vasopressin.

The compounds according to the invention can therefore be used for the preparation of medicaments, in particular of medicaments that are antagonists of the human $V_{1a}$ receptors for arginine-vasopressin and in particular, for some compounds, of the human $V_{1b}$ receptors for AVP.

Thus, according to another of its aspects, the subject of the invention is medicaments which comprise a compound of formula (I), or an addition salt thereof with a pharmaceutically acceptable acid.

These medicaments find their use in therapy, and are advantageously useful in disorders of the urogenital sphere in particular in the obstetric and gynecological fields, in particular as tocolytic agent or uterine relaxant or for controlling uterine hyperactivity, the contractions of the uterus before the pregnancy reaches full term, to control prenatal labour, or alternatively to control pre-preparatory labour for a caesarian delivery, to promote the growth of the fetus in utero, to reduce stress and anoxia at the time of contractions, to solve problems of sterility, fertility, to control births (veterinary use in particular), to control oestrus, weaning, the transfer and implantation of embryo during in vitro fertilization; to treat endometriosis, dysmenorrhea, and stress or urge urinary incontinence, benign prostatic hypertrophy, micturition disorders, urogenital infections, urinary lithiases and erectile dysfunction.

These medicaments are also useful in the treatment or prevention of various vasopressin-dependent conditions such as cardiovascular conditions like hypertension, pulmonary hypertension, cardiac insufficiency, myocardial infarction or coronary vasospasm, in particular in smokers, Raynaud's disease, PTCA (percutaneous transluminal coronary angioplasty), cardiac ischaemia, hemostasis disturbances, thrombosis; conditions of the central nervous system such as migraine, cerebral vasospasm, cerebral hemorrhage, cerebral oedemas and traumas, depression, anxiety, stress, emotional disorders, obsessive-compulsive disorder, schizophrenia, panic attacks, psychotic states, aggression, memory disorders, sleep disorders, cognitive disorders for example; conditions of the renal system such as renal vasospasm, necrosis of the renal cortex; nephrogenic diabetes insipidus; diabetic nephropathy; renal polycystic diseases, gastric system conditions such as gastric vasospasm, hepatocirrhosis, ulcers, pathology of vomiting, for example nausea, including nausea caused by chemotherapy, travel sickness. The compounds according to the invention may also be used in the treatment of sexual behaviour disorders; in women, the compounds according to the invention may be used to treat primary and secondary dysmenorrhea, premature labour or endometriosis. It is also possible to use the compounds according to the invention in the treatment of cancers such as small cell lung cancers or mammary cancers; hyponatremic encephalopathies; pulmonary syndrome, Meniere's disease; ocular hypertension, glaucoma, cataract; obesity; type I and II diabetes; atherosclerosis; metabolic syndrome; hyperlipidemia; insulin resistance; hypertriglyceridemia; in post-operative treatments, in particular after abdominal surgery; autism; hypercortisolemia; hyperaldosteronemia; pheochromocytomas; Cushing's syndrome; preeclampsia; micturition disorders; premature ejaculation.

The compounds according to the invention may also be used in the treatment or prevention of any pathology resulting from stress, such as fatigue and its syndromes, ACTH-dependent disorders, cardiac disorders, pain, modifications of gastric emptying, faecal excretion (colitis, irritable bowel syndrome, Crohn's disease), of acid secretion, hyperglycemia, immunosuppression, inflammatory processes (rheumatoid arthritis and osteoarthritis), multiple infections, septic shock, cancers, asthma, psoriasis, allergies and various neuropsychiatric disorders such as anorexia nervosa, bulimia, mood disorders, depression, anxiety, sleep disorders, panic states, phobias, obsession, pain perception disorders, (fibromyalgia), neurodegenerative diseases (Alzheimer's disease, Parkinson's disease, Huntington's disease), substance (alcohol or drug) dependence, withdrawal, hemorrhagic stress, muscle spasms, hypoglycemia. The compounds according to the invention may also be used in the treatment or prevention of chronic stress states such as immunodepression, fertility disorders, dysfunction of the hypothalamohypophyseal-adrenal axis.

The compounds according to the invention may also be used as psychostimulants, causing an increase in wakefulness, emotional reactivity towards the environment and facilitating adaptation.

The compounds according to the invention may finally be used in wound healing, in analgesia, in anxiolysis, in the prevention of pain, in the prevention of anxiety, depression, schizophrenia, autism, obsessive-compulsive syndromes, in maternal behaviour (facilitation of recognition and acceptance of the mother by the child) and social behaviour, memory; regulation of food and drink intake, drug dependence, withdrawal and sexual motivation; hypertension, hyponatremia, cardiac insufficiency, artherosclerosis, angiogenesis, tumour proliferation, Kaposi's sarcoma, regulating the storage of fat by the adipocyte, controlling hyperlipidemia, triglyceridemia and the metabolic syndrome.

According to another of its aspects, the present invention relates to pharmaceutical compositions comprising, as active ingredient, a compound according to the invention. These pharmaceutical compositions contain an effective dose of at least one compound according to the invention, a pharmaceutically acceptable salt and at least one pharmaceutically acceptable excipient.

The said excipients are chosen according to the pharmaceutical dosage form and the desired mode of administration, from the usual excipients which are known to persons skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its salts, may be adminstered in unit form for administration, mixed with conventional pharmaceutical excipients, to animals and to human beings for the prophylaxis or treatment of the above disorders or diseases.

The appropriate unit forms for administration comprise the forms for oral administration such as tablets, soft or hard gelatin capsules, powders, granules and oral solutions or suspensions, the forms for sublingual, buccal, intratracheal, intraocular or intranasal administration or for administration by inhalation, the forms for topical, transdermal, subcutaneous, intramuscular or intravenous administration, the forms for rectal administration and implants. For topical application, the compounds according to the invention may be used in creams, gels, ointments or lotions.

By way of example, a unit form for administration of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

By the oral route, the dose of active ingredient administered per day may be up to 0.01 to 100 mg/kg, in single or divided doses, preferably 0.02 to 50 mg/kg.

There may be specific cases when higher or lower dosages are appropriate; such dosages do not depart from the scope of the invention. According to usual practice, the dosage appropriate for each patient is determined by the doctor according to the mode of administration, the weight and the response of the said patient.

The present invention, according to another of its aspects, also relates to a method for treating the pathologies indicated above which comprises the administration, to a patient, of an effective dose of a compound according to the invention, or one of its pharmaceutically acceptable salts.

What is claimed is:
1. A compound corresponding to formula (I):

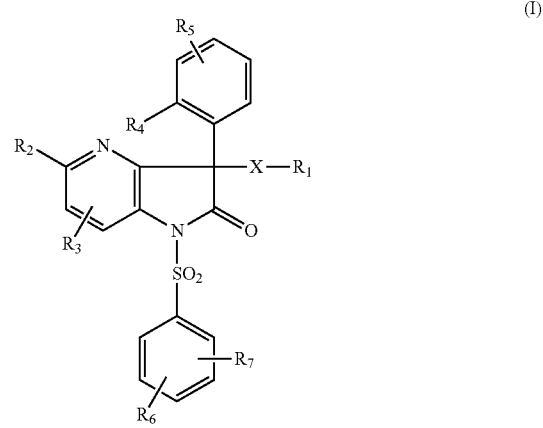

in which:
X represents a bivalent $(C_1-C_5)$alkylene radical that is unsubstituted or substituted once or several times on a carbon atom with a fluorine atom or with a $(C_1-C_3)$ alkyl;

$R_1$ represents:
  a group $-NR_8R_9$, or
  a piperidin-3-yl or piperidin-4-yl radical that is unsubstituted or substituted once or several times with a $(C_1-C_4)$alkyl, or a $(C_3-C_5)$cycloalkyl, it being possible for the carbon atoms to also be substituted with one or more fluorine atoms;

$R_2$ represents a hydrogen atom, a halogen atom, an Alk group, or an OAlk group;

$R_3$ represents a hydrogen atom, a halogen atom, an Alk group, or an OAlk group;

$R_4$ represents a hydrogen atom, a halogen atom, an Alk group, a hydroxyl, or an OAlk group;

$R_5$ represents a hydrogen atom, a halogen atom, an Alk group, a hydroxyl, or an OAlk group;

$R_6$ represents a hydrogen atom, a halogen atom, an Alk group, a hydroxyl, or an OAlk group;

R₇ represents a hydrogen atom, a halogen atom, an Alk group, a hydroxyl, or an OAlk group;

R₈ and R₉ each independently represent a hydrogen atom or a (C₁-C₄)alkyl;

or alternatively R₈ and R₉, together with the nitrogen atom to which they are attached, constitute a heterocyclic radical chosen from: azetidin-1-yl, pyrrolidin-1-yl, piperidin-1-yl, morpholin-4-yl, thiomorpholin-4-yl, piperazin-1-yl or perhydroazepin-1-yl, the said heterocyclic radical being unsubstituted or substituted once or several times with an amino, a hydroxyl, a (C₁-C₄)alkyl, a (C₃-C₅)cycloalkyl, or a (C₁-C₄) alkoxy, it being possible for the carbon atoms to also be substituted with one or more fluorine atoms; and Alk represents a (C₁-C₄)alkyl that is unsubstituted or substituted once or several times with a fluorine atom, or such a compound in the form of a base or of an acid addition salt, or an enantiomer or a racemic mixture thereof.

2. A compound according to claim 1, in which:

X represents a bivalent (C₃-C₄) alkylene radical that is unsubstituted or substituted once or several times on a carbon atom with a fluorine atom or with a (C₁-C₃) alkyl;

R₁ represents:
 a group —NR₈R₉, or
 a piperidin-4-yl radical;

R₂ represents an Alk group or an OAlk group;

R₃ represents a hydrogen atom;

R₄ represents a halogen atom;

R₅ represents a hydrogen atom;

R₆ represents a halogen atom or an OAlk group;

R₇ represents a hydrogen atom, an Alk group, or an OAlk group;

R₈ and R₉ together with the nitrogen atom to which they are attached constitute a heterocyclic radical chosen from: piperidin-1-yl, piperazin-1-yl, the said heterocyclic radical being unsubstituted or substituted once or twice with a fluorine atom, an amino, a hydroxyl, or a methyl;

Alk represents a (C₁-C₄)alkyl that is unsubstituted or substituted once or several times with a fluorine atom;

or such a compound in the form of a base or an acid addition salt, or an enantiomer or a racemic mixture thereof.

3. A compound according to claim 1, in which:

X represents a bivalent trimethylene or tetramethylene radical;

R₁ represents:
 a piperidin-1-yl, a piperazin-1-yl, a 4-methylpiperazin-1-yl, or a piperidin-4-yl;

R₂ represents a methyl or a methoxy;

R₃ represents a hydrogen atom;

R₄ represents a fluorine atom;

R₅ represents a hydrogen atom;

R₆ represents a chlorine atom, a methoxy, an isopropoxy, or a difluoromethoxy;

R₇ represents a hydrogen atom, a methyl, or a methoxy;

or such a compound in the form of a base or an acid addition salt, or an enantiomer or a racemic mixture thereof.

4. A compound according to claim 1, chosen from:

3-(2-fluorophenyl)-1-[(4-isopropoxyphenyl)sulphonyl]-5-methoxy-3-(3-piperazin-1-ylpropyl)-1,3-dihydro-2H-pyrrolo[3,2-b]pyridin-2-one;

3-(2-fluorophenyl)-5-methoxy-1-[(3-methoxyphenyl)sulphonyl]-3-(3-piperazin-1-ylpropyl)-1,3-dihydro-2H-pyrrolo[3,2-b]pyridin-2-one;

1-[(3-chlorophenyl)sulphonyl]-3-(2-fluorophenyl)-5-methoxy-3-(3-piperazin-1-ylpropyl)-1,3-dihydro-2H-pyrrolo[3,2-b]pyridin-2-one;

3-(2-fluorophenyl)-1-[(4-isopropoxyphenyl)sulphonyl]-5-methoxy-3-(3-piperidin-1-ylpropyl)-1,3-dihydro-2H-pyrrolo[3,2-b]pyridin-2-one;

3-(2-fluorophenyl)-5-methoxy-1-[(3-methoxyphenyl)sulphonyl]-3-(3-piperidin-1-ylpropyl)-1,3-dihydro-2H-pyrrolo[3,2-b]pyridin-2-one, isomer;

1-{[4-(difluoromethoxy)phenyl]sulphonyl}-3-(2-fluorophenyl)-5-methoxy-3-(3-piperidin-1-ylpropyl)-1,3-dihydro-2H-pyrrolo[3,2-b]pyridin-2-one;

1-[(3-chlorophenyl)sulphonyl]-3-(2-fluorophenyl)-5-methoxy-3-(3-piperidin-1-ylpropyl)-1,3-dihydro-2H-pyrrolo[3,2-b]pyridin-2-one;

3-(2-fluorophenyl)-1-[(4-isopropoxyphenyl)sulphonyl]-5-methoxy-3-(4-piperazin-1-ylbutyl)-1,3-dihydro-2H-pyrrolo[3,2-b]pyridin-2-one;

3-(2-fluorophenyl)-1-[(4-isopropoxyphenyl)sulphonyl]-5-methoxy-3-[3-(4-methylpiperazin-1-yl)propyl]-1,3-dihydro-2H-pyrrolo[3,2-b]pyridin-2-one;

3-(2-fluorophenyl)-1-[(4-isopropoxyphenyl)sulphonyl]-5-methoxy-3-[4-(4-methylpiperazin-1-yl)butyl]-1,3-dihydro-2H-pyrrolo[3,2-b]pyridin-2-one;

3-(2-fluorophenyl)-1-[(4-isopropoxyphenyl)sulphonyl]-5-methoxy-3-(3-piperidin-4-ylpropyl)-1,3-dihydro-2H-pyrrolo[3,2-b]pyridin-2-one;

3-(2-fluorophenyl)-1-[(4-isopropoxyphenyl)sulphonyl]-5-methoxy-3-(4-piperazin-1-ylbutyl)-1,3-dihydro-2H-pyrrolo[3,2-b]pyridin-2-one;

3-(2-fluorophenyl)-1-[(4-isopropoxyphenyl)sulphonyl]-5-methyl-3-(3-piperazin-1-ylpropyl)-1,3-dihydro-2H-pyrrolo[3,2-b]pyridin-2-one;

3-(2-fluorophenyl)-5-methoxy-1-[(4-methoxy-3-methylphenyl)sulphonyl]-3-(4-piperazin-1-ylbutyl)-1,3-dihydro-2H-pyrrolo[3,2-b]pyridin-2-one;

1-[(2,4-dimethoxyphenyl)sulphonyl]-3-(2-fluorophenyl)-5-methyl-3-(3-piperazin-1-ylpropyl)-1,3-dihydro-2H-pyrrolo[3,2-b]pyridin-2-one;

3-(2-fluorophenyl)-5-methoxy-1-[(4-methoxy-3-methylphenyl)sulphonyl]-3-(3-piperazin-1-ylpropyl)-1,3-dihydro-2H-pyrrolo[3,2-b]pyridin-2-one;

1-[(2,4-dimethoxyphenyl)sulphonyl]-3-(2-fluorophenyl)-5-methoxy-3-(3-piperazin-1-ylpropyl)-1,3-dihydro-2H-pyrrolo[3,2-b]pyridin-2-one;

3-(2-fluorophenyl)-1-[(4-methoxy-3-methylphenyl)sulphonyl]-5-methyl-3-(3-piperazin-1-ylpropyl)-1,3-dihydro-2H-pyrrolo[3,2-b]pyridin-2-one;

1-[(2,4-dimethoxyphenyl)sulphonyl]-3-(2-fluorophenyl)-5-methoxy-3-(4-piperazin-1-ylbutyl)-1,3-dihydro-2H-pyrrolo[3,2-b]pyridin-2-one;

3-(2-fluorophenyl)-1-[(4-isopropoxyphenyl)sulphonyl]-5-methyl-3-[3-(4-methylpiperazin-1-yl)propyl]-1,3-dihydro-2H-pyrrolo[3,2-b]pyridin-2-one;

3-(2-fluorophenyl)-5-methoxy-1-[(4-methoxy-3-methylphenyl)sulphonyl]-3-[4-(4-methylpiperazin-1-yl)butyl]-1,3-dihydro-2H-pyrrolo[3,2-b]pyridin-2-one;

or such a compound in the form of a base or of an acid addition salt, or an enantiomer or a racemic mixture thereof.

5. A method for preparing a compound of formula (I) according to claim 1, comprising:

reacting a compound of formula:

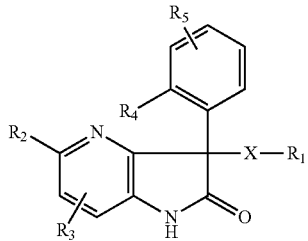

(II)

in which X, $R_1$, $R_2$, $R_3$, $R_4$ and $R_5$ are as defined in claim 1, in the presence of a base, with a sulphonyl halide of formula:

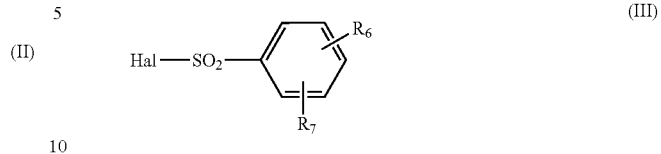

(III)

in which $R_6$ and $R_7$ are as defined in claim 1 and Hal represents a halogen atom.

6. A pharmaceutical composition comprising a compound of claim 1 and at least one pharmaceutically acceptable excipient.

* * * * *